United States Patent
Slepicka

(10) Patent No.: US 8,654,318 B2
(45) Date of Patent: Feb. 18, 2014

(54) CASSETTE-BASED METHOD AND APPARATUS FOR MEASURING THE PRESENCE AND CONCENTRATION OF PHARMACEUTICAL SUBSTANCES IN A MEDICAL FLUID

(75) Inventor: James S. Slepicka, Genoa City, WI (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/346,249

(22) Filed: Jan. 9, 2012

(65) Prior Publication Data

US 2012/0105850 A1  May 3, 2012

Related U.S. Application Data

(63) Continuation of application No. 11/773,581, filed on Jul. 5, 2007, now Pat. No. 8,094,307.

(51) Int. Cl.
*G01N 33/48* (2006.01)
*G01J 4/00* (2006.01)

(52) U.S. Cl.
USPC ............. 356/39; 356/244; 356/364; 356/440

(58) Field of Classification Search
USPC ............... 356/36–42, 243.1–246, 335–343
See application file for complete search history.

(56) References Cited

U.S. PATENT DOCUMENTS

| | | | |
|---|---|---|---|
| 5,109,849 A | 5/1992 | Goodman et al. | |
| 5,386,819 A | 2/1995 | Kaneko et al. | |
| 5,650,847 A * | 7/1997 | Maltsev et al. | 356/336 |
| 5,777,740 A | 7/1998 | Lacey et al. | |
| 6,433,876 B1 * | 8/2002 | Kuhn | 356/516 |
| 6,586,193 B2 * | 7/2003 | Yguerabide et al. | 506/3 |
| 2005/0099624 A1 | 5/2005 | Staehr et al. | |
| 2006/0287887 A1 | 12/2006 | Hutchinson | |
| 2007/0023334 A1 * | 2/2007 | Hallstadius et al. | 210/94 |

FOREIGN PATENT DOCUMENTS

| | | |
|---|---|---|
| EP | 1332720 A | 8/2003 |
| EP | 1387161 A | 2/2004 |
| EP | 1609411 A | 12/2005 |
| WO | 2004/033003 A | 4/2004 |

OTHER PUBLICATIONS

May 2005 Article: "New Approach to the Measurement of Refractive Index", L.M. Bali et al., Optical Engineering, vol. 44, No. 5, pp. 058002-1 to 058002-6, Publ. May 2005.
"Development of a Non-Invasive Polarimetric Glucose Sensor", Roger J. McNichols, et al., IEEE Lasers and Electro-Optics Society (LEOS) Newsletter, vol. 12, #2, Apr. 1998.
International Search Report for PCT/US2008/068909 dated Jan. 5, 2010.

* cited by examiner

*Primary Examiner* — Tara S Pajoohi Gomez
(74) *Attorney, Agent, or Firm* — K&L Gates LLP

(57) ABSTRACT

A medical fluid delivery system includes a medical fluid delivery machine including a light source configured to generate a light beam; a polarizer configured to receive the light beam and to allow a portion of the light beam within the medical fluid to be transmitted through the polarizer, a photodetector to provide a measurement of an intensity of the light beam transmitted through a medical fluid and the polarizer; a medical fluid cassette operating with the medical fluid machine to pump the medical fluid, the medical fluid cassette loaded onto the medical fluid delivery machine such that the light source resides on a first side of the cassette and the photodetector resides on a second side of the cassette; and a computer configured to use the measurement of the intensity to determine whether the medical fluid can be delivered to a patient.

22 Claims, 13 Drawing Sheets

CASSETTE-BASED METHOD AND APPARATUS FOR MEASURING THE PRESENCE AND CONCENTRATION OF PHARMACEUTICAL SUBSTANCES IN A MEDICAL FLUID

PRIORITY CLAIM

This application claims priority to and the benefit as a continuation application of U.S. patent application Ser. No. 11/773,581, filed Jul. 5, 2007, entitled, "Method and Apparatus for Measuring the Presence and Concentration of Pharmaceutical Substances in a Medical Fluid Administered by a Medication Delivery System", the entire contents of which are hereby incorporated by reference and relied upon.

BACKGROUND

The present disclosure relates to healthcare and medication delivery systems. In particular, the present disclosure relates to testing and controlling the quality of medical fluids being delivered to a patient using healthcare/medication delivery systems.

Complex medical fluids are often administered to a patient through a variety of different medication delivery systems. For example, a medication delivery system, such as a dialysis machine for performing peritoneal dialysis for a patient that may be experiencing decreased or total loss of kidney function, uses a dialysis solution to remove waste products from the bloodstream. In another example, a medication delivery system, such as an infusion pump, delivers a liquid drug or medical fluid such as morphine or the like to a patient based upon parameters entered into the medication delivery system. The medical fluid may be a homogenous liquid, a mixed solution, or a solution that includes particulates in a buffer liquid. The presence of the medication, or the correct concentration of the medication, in the solution being delivered to a patient is important to prevent medical errors. An error could include the administration of the wrong drug or an improper dose of the correct drug.

A problem associated with peritoneal dialysis, for example, is an improperly mixed solution delivered to a patient. The medical fluid, or dialysate, for peritoneal dialysis can be packaged in a dual-chamber bag, in which one chamber includes a buffer solution and the other chamber includes a concentrated glucose solution. The chambers of the bag are separated by a peel seal that is ruptured upon pressure exerted on one of the chambers. The pH value for both the buffer solution and the glucose solution, or pharmaceutical substance, are potentially harmful to the patient, but the resulting pH value of a completely mixed fluid containing both the buffer and glucose solutions is physiologically compatible. Accordingly, the failure of the peel seal to rupture completely may result in a mixed medical fluid containing an undesirable proportion of buffer solution to glucose solution. It is therefore desirable to test the medical fluid being transferred from the dual chamber bag to the medication delivery system prior to the medical fluid being delivered to the patient.

Several testing mechanisms exist for identifying pharmaceutical substances within a medical fluid and the concentration of such substances. Some testing mechanisms are integrated within the medication delivery system as permanent components. These integrated testing mechanisms are typically invasive. That is, the sensors used to detect various aspects of the medical fluid are in direct contact with the medical fluid. Between uses, these medication delivery systems are typically cleaned or sterilized. However, without proper cleaning or sterilization, the invasive testing mechanisms may contaminate subsequent medical fluids and patients.

Non-invasive testing mechanisms are also used for identifying pharmaceutical substances within a medical fluid and the concentration of such substances. The non-invasive sensors do not contact the medical fluid directly. Non-invasive testing mechanisms are typically less accurate than the invasive testing mechanisms due in part to the geometry and material of the barrier between the medical fluid and the sensors of the non-invasive testing mechanism.

A need accordingly exists for a sterile testing mechanism to test the for the presence or concentration, or both, of pharmaceutical substances in medical fluids to be administered to a patient. A need also exists for an inexpensive, single-use testing mechanism. Yet another need exists for an accurate testing mechanism for testing the presence or concentration, or both, of pharmaceutical substances in medical fluids to be administered. A need further exists for a method and apparatus for controlling the distribution of pharmaceutical substances in medical fluids once the presence or concentration of the substance in the medical fluid has been measured.

SUMMARY

The present disclosure provides multiple embodiments of a testing mechanism that tests the quality of a medical fluid to be dispensed to a patient.

In one embodiment, the testing mechanism includes a light source located adjacent to a medical fluid, the medical fluid within a medical delivery system and the light source configured to generate a light beam directed through a portion of the medical delivery system and the medical fluid, a first polarizer configured to receive the light beam and to allow a portion of the light beam optically rotated by a pharmaceutical substance within the medical fluid to be transmitted through the first polarizer, a photodetector to provide a measurement of an intensity of the portion of the light beam transmitted through the first polarizer, and a computer configured to use the measurement of the intensity to perform a matching check to determine whether the pharmaceutical substance is present in the medical fluid.

Another embodiment of a testing mechanism includes a light source located adjacent to a medical fluid, the fluid within a medical delivery system and the light source configured to generate a light beam having a propagation axis, a prism having an incidence surface, a reflective surface, and an interface surface for receiving, reflecting and refracting the light beam from the light source, a photodetector configured to receive and measure at least one of an intensity and a position of the light beam transmitted through the medical fluid and a portion of the medical delivery system, the photodetector configured to generate an output signal representing at least one of the intensity and position of the light beam, and a computer operatively connected to the photodetector, the computer configured to receive the output signal and perform a matching check to determine whether the medical fluid includes a pharmaceutical substance.

Another embodiment is a testing mechanism that includes a light source positioned adjacent to a medical fluid, the medical fluid within a medication delivery system and the light source configured to generate a polarized light beam directed through the medical fluid and a portion of the medical delivery system, a photodetector for providing a measurement of at least one of intensity, relative position, and relative optical rotation, of the light beam that was transmitted through the medical fluid and the portion of the medical fluid, and a memory configured to store signals from the photodetector or results from calculations performed on the signals, including signals or calculations from a baseline measurement, the baseline measurement optionally including a portion of the medical delivery system present between the light source and the photodetector. The testing mechanism also includes a computer operably connected to the memory and configured to use the signals or results stored in the memory to perform a matching check with respect to the baseline measurement to determine at least one of: (i) whether a pharmaceutical substance is present in the medical fluid; and (ii) a concentration of the pharmaceutical substance present in the medical fluid.

Another embodiment is a method of testing a medical fluid. The method includes steps of furnishing a first medical fluid in a medical container, the first medical fluid having an expected concentration of at least one pharmaceutical substance, calibrating a testing device for optical properties using light rotation properties or refractive index of at least two test concentrations of the at least one pharmaceutical substance in the first medical fluid, calculating a lookup table of optical property values for a plurality of concentrations of the at least one pharmaceutical substance in the first medical fluid, storing the lookup table of optical activity values in a computer or in a memory accessible to the computer, and optionally, calibrating the testing device for an optical property of at least a portion of the medical container. The method also includes steps of introducing a second medical fluid having an expected concentration of at least one pharmaceutical substance into the testing device, wherein the second medical fluid may be the same as the first medical fluid or may be different, testing the second medical fluid for a presence of the at least one pharmaceutical substance using the optical property and determining a concentration of the at least one pharmaceutical substance, and determining whether the determined concentration is within a desired range for the second medical fluid.

Additional features and advantages are described herein, and will be apparent from, the following Detailed Description and the figures.

DETAILED DESCRIPTION OF THE PRESENTLY PREFERRED EMBODIMENTS

Figure 1A:
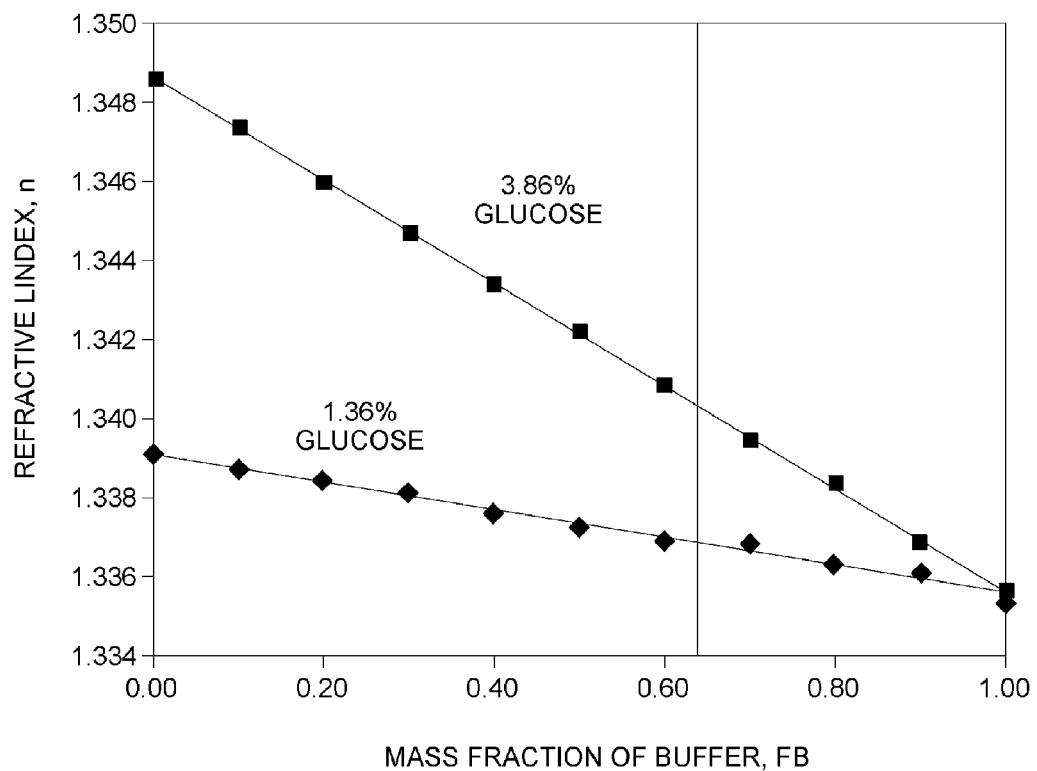
FIGS. 1A-C are graphs depicting how optical values are correlated with concentrations of a particular pharmaceutical substance.

Delivery of medical fluids to a patient may be performed within a healthcare facility by a caregiver or elsewhere by the patient. A medication delivery system is typically used to assist in the delivery of a medical fluid to a patient. It is important that the proper medical fluid at the proper dose or concentration is delivered to the patient by the medication delivery system. Accordingly, a testing mechanism of the present disclosure is used in cooperation with medication delivery systems to test the medical fluid to ensure that the proper medication or concentration of the medication, or both, is delivered to the patient. The testing mechanism may be configured to test for the presence or absence of a particular pharmaceutical substance within the medical fluid or to test for the concentration of a particular pharmaceutical substance within the medical fluid.

In an embodiment, the testing mechanism is configured to test for pharmaceutical substances such as glucose, morphine, creatine, urea, or Factor-VIII, or the like. In another embodiment, the testing mechanism is configured to test for the presence or concentration, or both, of a pharmaceutical substance that a user specifies during the start-up process of the medication delivery system. The testing mechanism tests the medical fluid prior to the medical fluid being administered to the patient to prevent delivery of a medical fluid not suitable for the patient. The testing mechanism may be located upstream from the medication delivery system, may be incorporated within the medication delivery system, may be attached to the medication delivery system, or may be located downstream from the medication delivery system relative to the container containing the medical fluid.

A light property, the refractive index of light or optical rotation of light, is used for these determinations. In particular, one embodiment of the invention uses the effect of a substance on the refractive index of a solution to determine the substance and the concentration of the substance. In another embodiment, the effect of a substance on the ability of a solution to rotate light is used to determine the substance and its concentration. In refractive index embodiments, a beam of light propagating through one material is directed onto the surface of another material at an angle other than 90°. Part of the beam will thus reflect off the interface and the rest is transmitted through a second material. The propagation direction of the transmitted beam will also change. The amount that the direction changes depends on the refractive index of the materials as given by Snell's law $$n_1 \sin(\theta_1) = n_2 \sin(\theta_2), \quad \text{(Equation 1)}$$

where $n_1$ is the refractive index of the first material, $\theta_1$ is the angle of incidence with respect to the normal of the interface plane of the two materials, $n_2$ is the refractive index of the second material, and $\theta_2$ is the new angle of propagation. Solving for $\theta_2$, $$\theta_2 = \arcsin[(n_1/n_2)\sin(\theta_1)]. \quad \text{(Equation 2)}$$

The new propagation direction is influenced by the ratio of refractive indices. Thus, for a constant value of $n_1$, a change in $n_2$ will affect the propagation direction. In the case of dialysis solutions, glucose is present in one chamber of a flexible container and buffer solution is present in the other chamber. Aqueous glucose has a high refractive index for a fluid, 1.36 in a 20% w/w concentration, compared to a value of 1.333 for water. The addition of glucose to water, or other fluid of lesser refractive index will increase the refractive index of the mixture. Therefore, the presence of glucose can be detected by measuring the change in direction of beam of light propagated and sent through the solution.

Measurements of refractive index of two different solutions of glucose as a function of their mass fraction when mixed with buffer solution are plotted in FIG. 1A. In this instance, it is easy to distinguish between solutions with two different concentrations of glucose. It is also easy to distinguish between solutions with different ratios of buffer solution to glucose solution. This ability will enable medical professionals or technicians to distinguish between the relative mixtures of solutions. In other embodiments, an amount of light is rotated in a particular direction by a solution, of an amount of light is refracted or reflected in a known manner. In these embodiments, the amount of light detected at a particular location, as a result of the rotation, refraction, or reflection is detected by one or more photodetectors. The amount of light detected at a particular angle or location is indicative of a substance or a particular quantity of the substance in a solution.

Figure 1B:
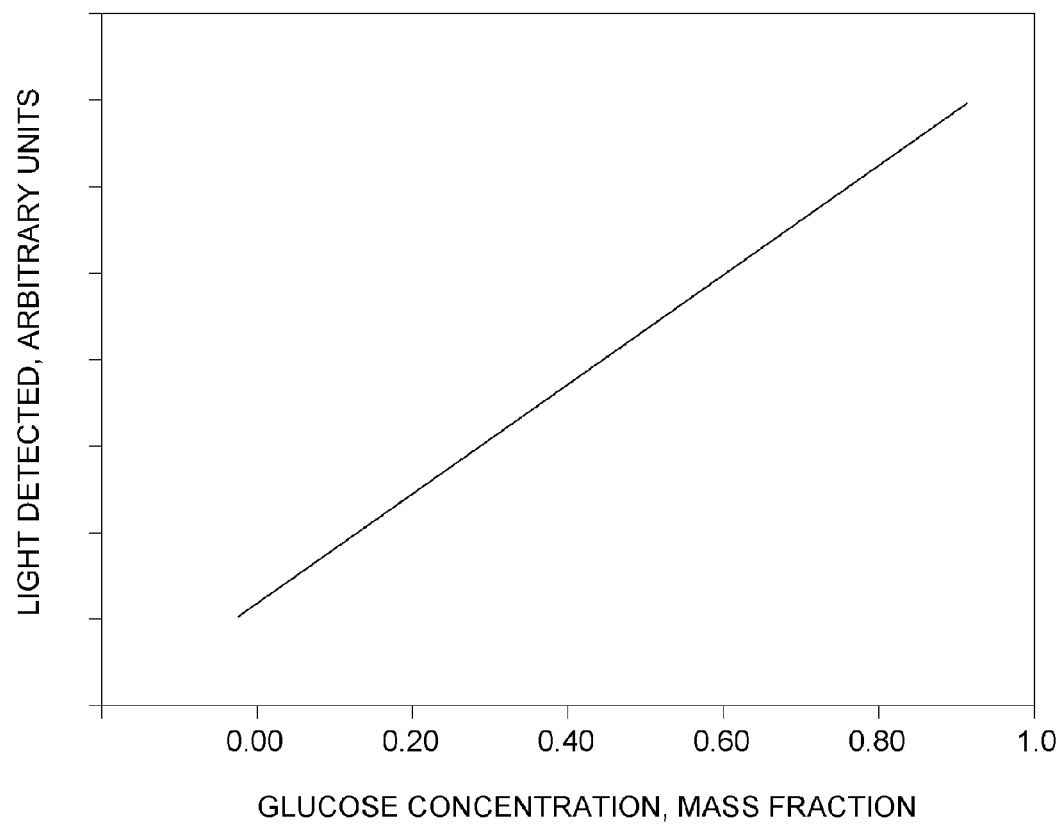
Figure 1C:
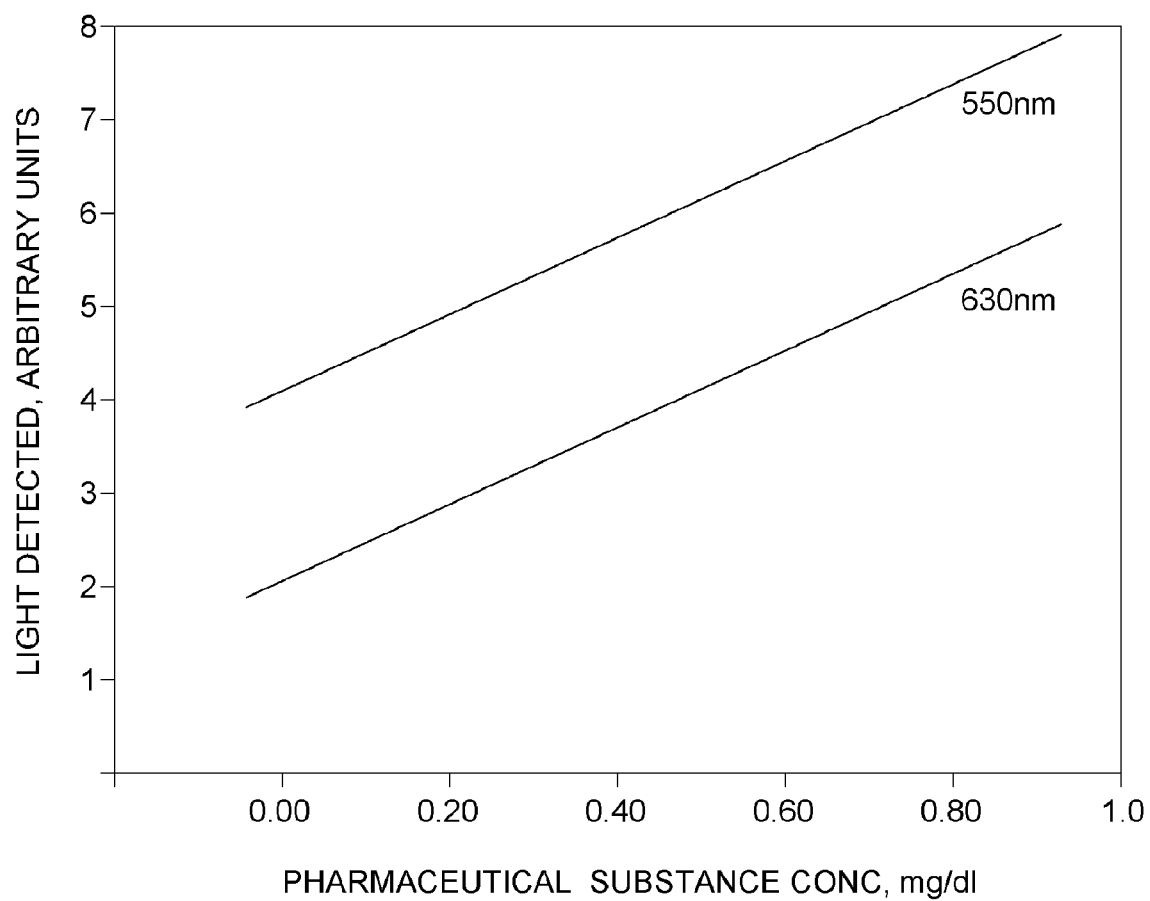

FIGS. 1B and 1C are graphs depicting these principles. In FIG. 1B, a quantity of light is detected at a particular location, the quantity dependent on the concentration of substance in a solution, such as a mass fraction of glucose or other pharmaceutical substance. In FIG. 1C, a quantity of light is again detected at a particular location, the quantity dependent on the concentration of pharmaceutical substance in solution. In this case, the calibration test is run with two incident light of two different wavelengths, 550 nm and 630 nm. Different results are obtained for the two different wavelengths. These differences may be taken into account when designing practical testing instruments or mechanisms, for qualities such as interference and relative sensitivity of the instrument.

A medication delivery system using these principles includes a microprocessor computer or controller that controls the operation of the testing mechanism, and a memory element, accessible to the computer, that stores the test data. The memory element used to store test data may be incorporated within the microprocessor or within the testing mechanism. The computer provides an output signal to the medication delivery system based upon the test or tests performed by the testing mechanism. For example, if the testing mechanism identifies a pharmaceutical substance not intended to be in the medical fluid, the computer generates an output signal to the medication delivery system to provide an alert or to prevent the medical fluid from being delivered to the patient. If the testing mechanism determines that the pharmaceutical substance is not present in the medical fluid being tested, the computer generates an output signal to the medication delivery system to provide an alert or prevent the medical fluid from being delivered to the patient. If the testing mechanism determines that the concentration of the pharmaceutical substance is outside an acceptable range for the concentration, the computer generates an output signal to the medication delivery system or to an operator to provide an alert or to prevent the medical fluid from being delivered to the patient.

Figure 2:
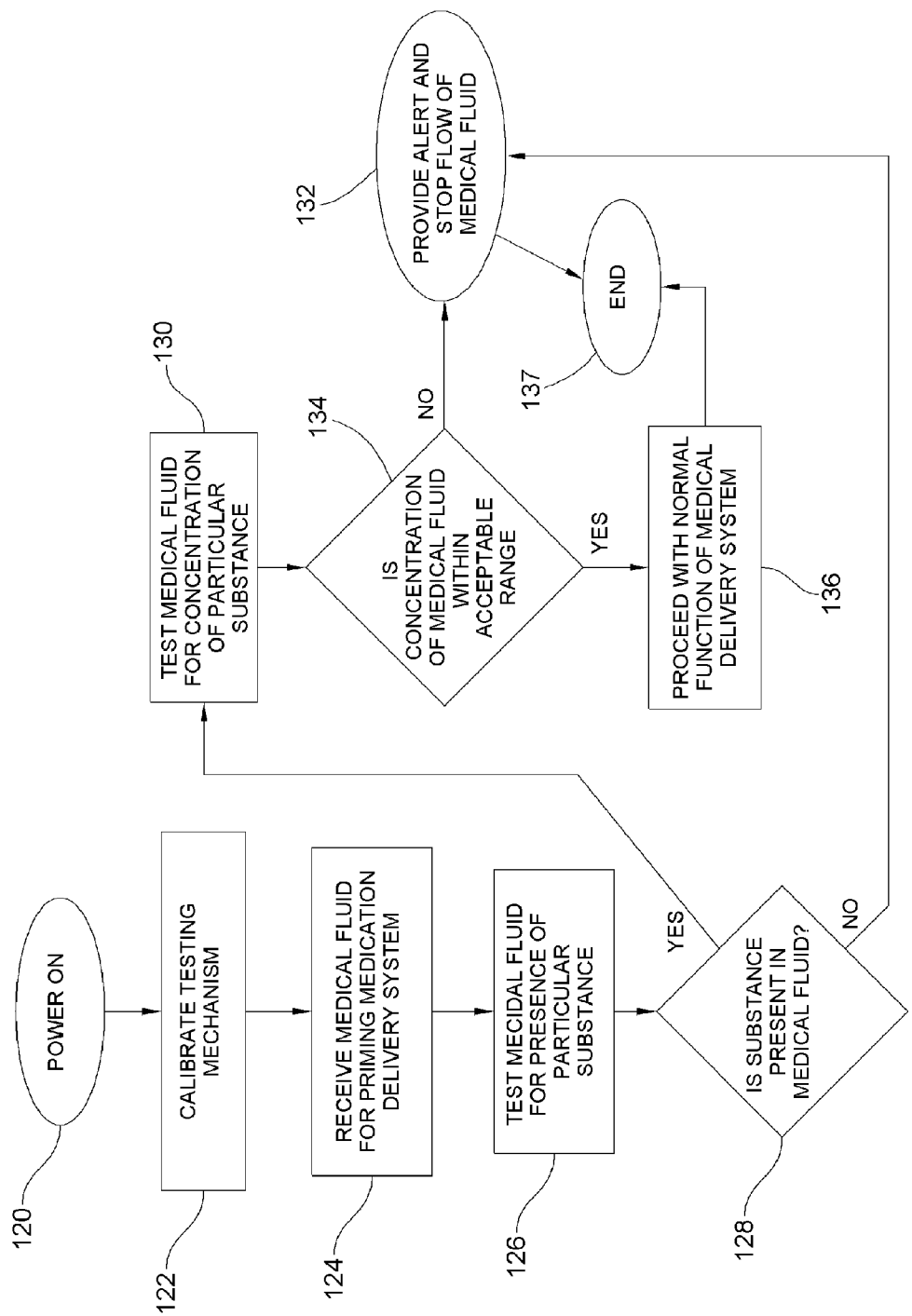
FIG. 2 is a flow diagram of an embodiment of a process for testing a medical fluid for a particular pharmaceutical substance.

FIG. 2 illustrates a process controlling a testing mechanism for testing a medical fluid being delivered to a patient. In the illustrated embodiment, the apparatus is testing for a particular pharmaceutical substance that is assumed to be within the medical fluid. For example, a dialysis machine delivers dialysate solution to the patient, wherein the dialysate delivered in each successive operation of the dialysis machine contains glucose molecules. The process of FIG. 2 is thus configured to test for the presence or absence of glucose molecules in each successive test of the medical fluid. The process of FIG. 2 is not limited to glucose testing, however, and may be used to test for other possible or assumed pharmaceutical substances. Once a container containing a medical fluid is connected to a medication delivery system, the medication delivery system is powered on, as shown by step 120. After the medication delivery system is powered on, the computer causes the testing mechanism to be calibrated or reset, as shown in step 122. After the medication delivery system is powered on, the medication delivery system receives the medical fluid to prime the system, as shown by step 124. As the medical fluid primes the medication delivery system, the testing mechanism performs at least one test of the medical fluid to determine the presence or absence of the particular pharmaceutical substance, as shown by step 126. This test may use polarized light to measure rotation of light by a pharmaceutical substance in the medical fluid. Alternatively, the test may measure the refractive index of a solution of a pharmaceutical substance in order to determine the concentration of the substance.

In step 128, the computer receives a signal from the testing mechanism and determines if the particular pharmaceutical substance is present in the medical fluid. If the computer determines that the particular pharmaceutical substance is present in the medical fluid, the computer outputs a signal for the testing mechanism to proceed with testing the medical fluid again to determine the concentration of the particular pharmaceutical substance, as shown in step 130. If the medical fluid is tested and the particular pharmaceutical substance is not present in the medical fluid, the computer outputs a signal to provide an alert to the user or to prevent delivery of the medical fluid to the patient, as shown by step 132.

In step 130, the computer outputs a signal to the testing mechanism to proceed with testing the medical fluid to determine the concentration of the particular pharmaceutical substance. In an embodiment, the test for the concentration of the particular pharmaceutical substance in step 130 includes a separate test of the medical fluid than the one performed in step 126. In an alternative embodiment, the test for the concentration of the particular pharmaceutical substance in step 130 is incorporated into the test of step 126. Here, a single test results in the determination of both the presence or absence of the particular substance and the concentration of the particular substance if present. Once the concentration of the pharmaceutical substance has been determined in step 130, the computer performs a matching check to determine if the concentration of the substance in the medical fluid is within an acceptable range, as shown by step 134. In an embodiment, the computer compares the tested concentration with a pre-programmed concentration range for the pharmaceutical substance. In another embodiment, the computer compares the tested concentration with an acceptable concentration range provided which the user inputs prior to the priming step 124. In yet another embodiment, the computer is operatively connected to a pharmaceutical database, which provides an acceptable concentration range of the pharmaceutical substance for the matching check.

If the computer determines in step 134 that the concentration of the pharmaceutical substance in the medical fluid is within an acceptable range, the computer outputs a signal to the medication delivery system to proceed with normal function of the system, as shown by step 136. If the computer determines in step 134 that the concentration of the pharmaceutical substance in the medical fluid is outside an acceptable range, the computer outputs a signal to provide an alert to the user or to prevent delivery of the medical fluid to the patient, as shown in step 132. The sequence then ends as indicated by step 137.

Figure 3A:
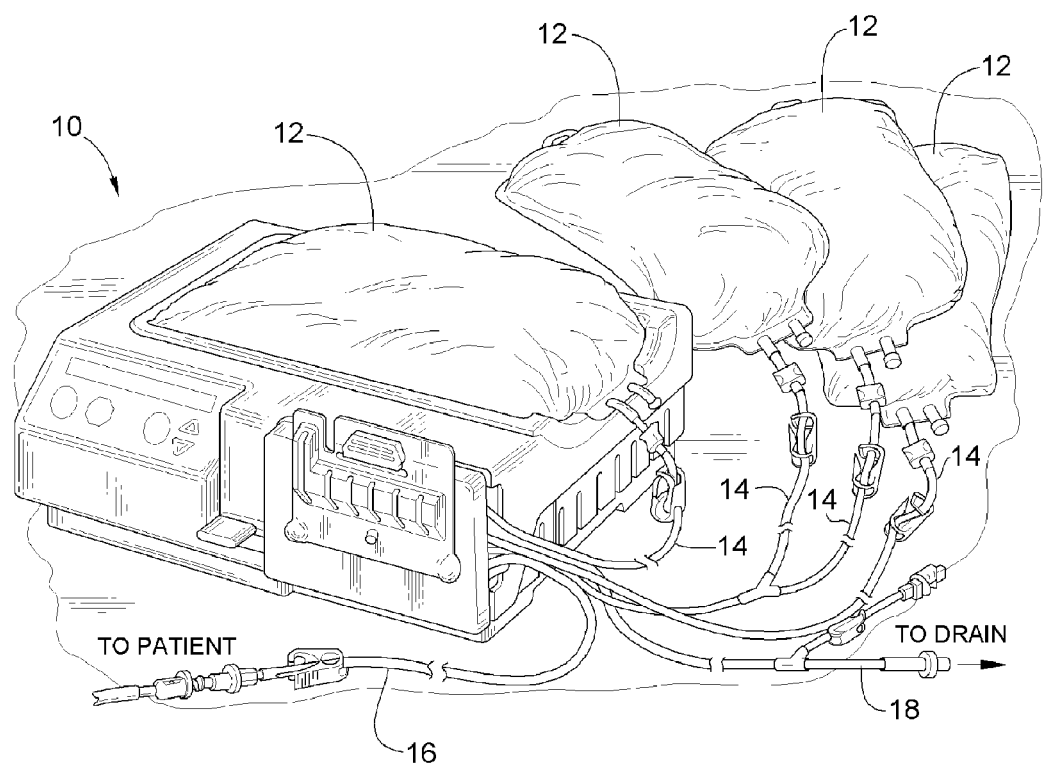
FIG. 3A is a top perspective of one embodiment of a medication delivery system.

In one embodiment, a testing mechanism for testing a medical fluid is incorporated with a medication delivery system such as a dialysis machine 10, illustrated in FIG. 3A. In another embodiment, a testing mechanism for testing a medical fluid is incorporated within a different medication delivery system such as an infusion pump (not shown). The testing mechanisms of the present disclosure are illustrated and described as cooperating with a dialysis machine, but it should be understood by one skilled in the art that the dialysis machine is an exemplary medication delivery system and the testing mechanism can be used in cooperation with any medication delivery system that delivers a medical fluid to a patient. It should be understood by one skilled in the art that the testing mechanisms of the present disclosure can be incorporated within a medication delivery system, or the testing mechanisms of the present disclosure can be formed as devices separate from the medication delivery system, but which maintain an operative connection to the medication delivery system. A medical delivery system for a particular medical fluid may include a bag or container in which the medical fluid is typically or commercially furnished, and may include integral or appended tubing for delivery to the patient.

A plurality of medication containers 12 containing medical fluid are attached to the dialysis machine 10, as shown in FIG. 3A. In an embodiment, each medication container 12 contains the same medical fluid. For example, each medication container 12 contains a dialysis solution, or dialysate, containing glucose molecules. In another embodiment, each medication container 12 includes different medical fluids that are combinable within the dialysis machine 10 prior to being delivered to a patient. A disposable line set 14 operatively connects each medication container 12 to the dialysis machine 10. A line 16 leading to the patient, formed of a disposable tube, delivers the medical fluid from the dialysis machine 10 to the patient (not shown). A drain line 18 formed of a disposable tube directs spent dialysate and blood waste products from the dialysis machine 10 to a drain container (not shown).

Figure 3B:
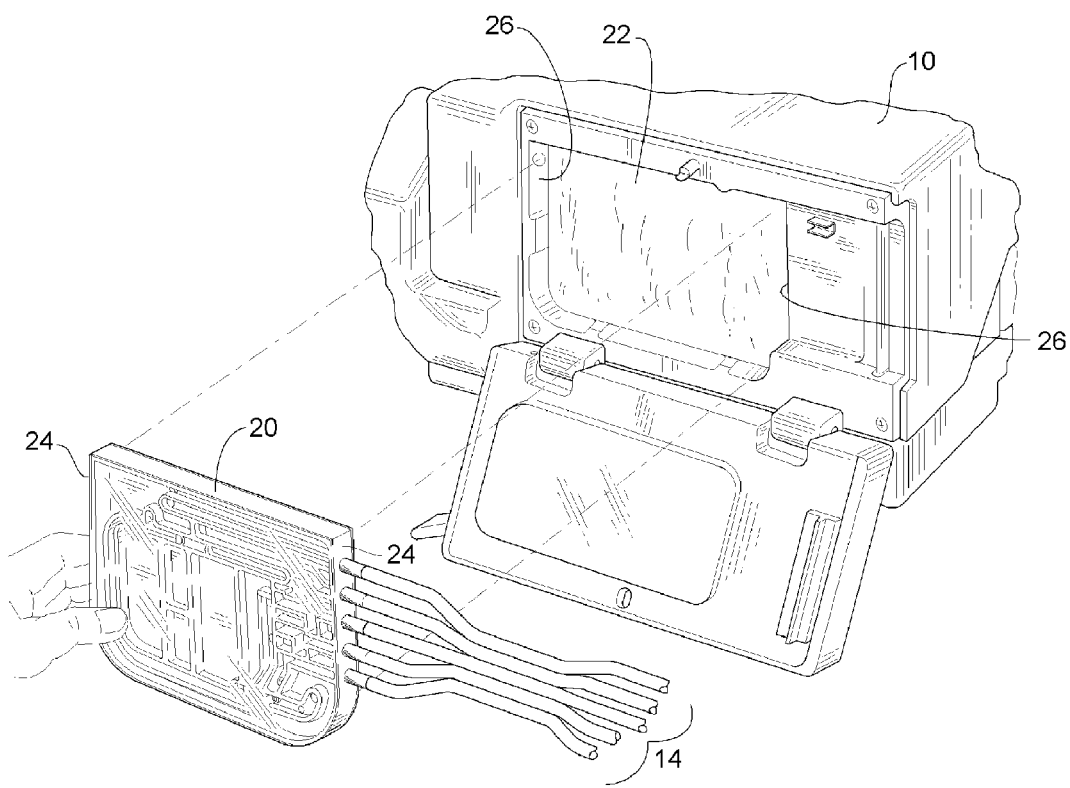
FIG. 3B is a magnified view of a portion of the medication delivery system of FIG. 3A.
Figure 3C:
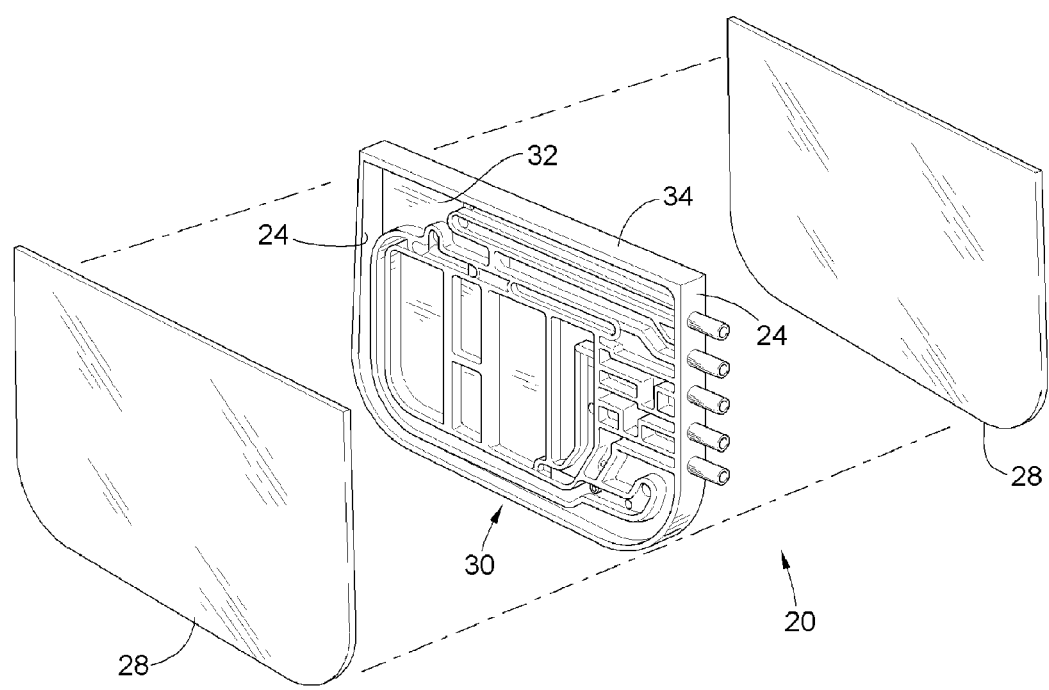
FIG. 3C is an exploded view of one embodiment of a disposable medical fluid cassette.
Figure 3D:
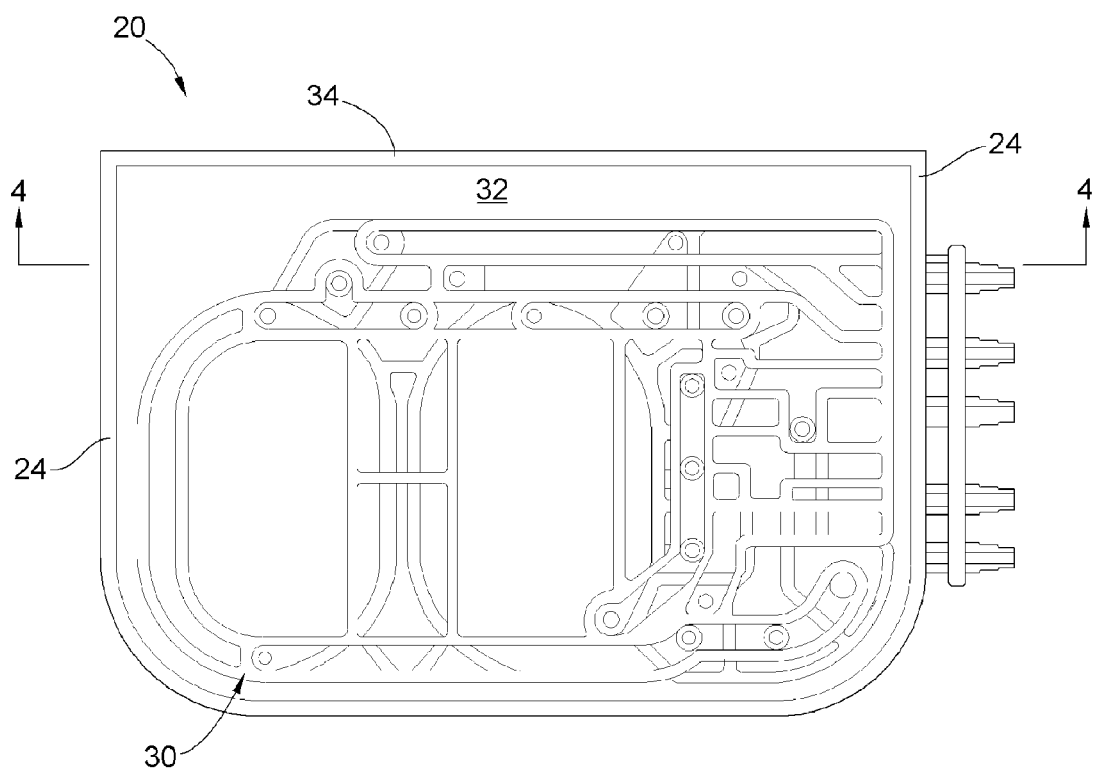
FIG. 3D is a front view of the disposable medical fluid cassette of FIG. 3C.

The dialysis machine 10 receives a disposable fluid containment device, such as a cassette 20 or a portion of the line set 14, to which the medication containers 12 are connected, as illustrated in FIG. 3B. The dialysis machine 10 includes a recessed area 22 for receiving the disposable cassette 20. The recessed area 22 is sized and shaped to provide a snug fit with the disposable cassette 20 to ensure the cassette 20 is properly aligned within the recessed area 22. In particular, the opposing side walls 24 of the cassette 20 fit snuggly within opposing inner walls 26 of the recessed area 22. As shown in FIGS. 3C and 3D, the cassette 20 includes a pair of flexible membranes 28 attached to opposing surfaces of a rigid structure 30. The flexible membranes 28 are operatively attached to the rigid structure 30 to provide, for example, pumping movement to allow the medical fluid received from the medication containers 12 and delivered to the patient.

Within the rigid structure 30, an elongated passageway 32 is formed adjacent to an outer wall 34, as illustrated in FIGS. 3C and 3D. The elongated passageway 32 receives medical fluid from the medication containers 12. The elongated passageway 32 extends in a substantially linear manner between the opposing side walls 24 and the outer wall 34 of the cassette 20. The thickness of each of the opposing side walls 24 is about 2 mm. The rigid structure 30 of the cassette is formed of acrylic. Other thicknesses and other materials may be used, so long as the materials are relatively transparent to the wavelength of light being used. The side walls 24 in one embodiment are substantially transparent, allowing an optical light beam to pass through and between the opposing side walls 24.

Figure 4:
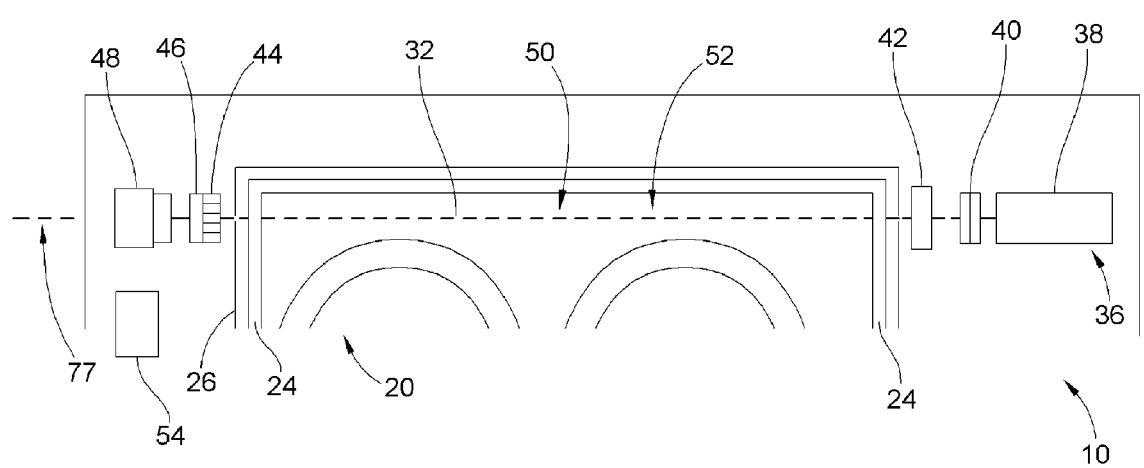
FIG. 4 is a cross sectional view of the cassette of FIG. 3D along line IV-IV including one use or application of a testing mechanism of the present disclosure.

As illustrated in FIG. 4, a testing mechanism 36 is integrated within dialysis machine 10. The testing mechanism 36 provides a non-invasive testing process of a medical fluid received by the dialysis machine 10. In an embodiment, the testing mechanism 36 for testing medical fluids uses optical polarization rotation and includes a light source 38, a first polarizer 40, polarization rotator 42, a narrow pass filter 44, a second polarizer 46, and a photodetector 48. The light source 38 is any light source 38 capable of generating a directed light beam 50. In an embodiment, the light source 38 is a laser that generates a polarized light beam 50 with a single polarization orientation, such as a vertical or horizontal polarization. In a further embodiment, the light source 38 generates a randomly polarized light beam 50. In another embodiment, the light source 38 is a laser light emitting diode ("LED"). In yet another embodiment, the light source 38 is a fluorescent light, or any other type of randomly polarized light capable of producing a light beam 50.

It should be understood by one skilled in the art that any light source capable of producing a narrow beam of light can be used. One skilled in the art will recognize that light beam 50 may have a number of different wavelengths or orientations. Narrow pass filter 44 allows light having a predefined wavelength to pass therethrough. The He—Ne laser light source in one embodiment generates a light beam having a green wavelength of 543 nm or a red wavelength of 633 nm. In another embodiment, a diode laser light source generates light beams having wavelengths of 670 nm and 830 nm. In general, light with a wavelength from about 350 nm to about 900 nm may be used, but light with other wavelengths may also be used. Light beams detrimental to the medical fluid being tested should not be used.

In an embodiment, the light beam 50 is transmitted through the first polarizer 40, as shown in FIG. 4. The first polarizer 40 polarizes the light beam 50 to produce light in a single, predetermined orientation. The first polarizer 40 prevents or blocks portions of the light beam 50 having orientations other than the predetermined orientation of the first polarizer 40 from passing therethrough. A first polarizer 40 is not needed when the light source 38 is a laser or other type of light source that provides a light beam 50 polarized in a single orientation, such as a beam having a vertically oriented wavelength.

In the illustrated embodiment, the polarized light beam 50 leaving the first polarizer 40 passes through a polarization rotator 42, as shown in FIG. 4. The polarization rotator 42 can be a liquid crystal device. The polarization rotator 42 rotates the polarization of the light beam 50 prior to the light beam being transmitted into the cassette 20. Rotation of the polarization of the light beam 50 compensates for the adverse effects that cassette 20 can cause to light beam 50, such as rotation of the light beam. These effects are discussed in more detail below.

Once the light beam 50 is transmitted through the polarization rotator 42, the light beam 50 enters the passageway 32 of cassette 20 through one of the side walls 24, as shown in FIG. 4. FIG. 4 shows a gap between side walls 24 of the cassette 20 and the inner wall 26 of the dialysis machine 10 for illustrative purposes only. In one embodiment, side walls 24 of cassette 20 are in an abutting or aligned relationship relative to inner walls 26 of recessed area 22 of dialysis machine 10 to ensure proper orientation of passageway 32 and side walls 24 between light source 38 and the photodetector 48. In one embodiment, cassette 20 is aligned within the recessed area 22 of dialysis machine 10 such that opposing side walls 24 of cassette 20 are aligned substantially normal relative to propagation axis 77 of light beam 50.

After light beam 50 exits the second of the two side walls 24, the light beam passes through a narrow pass filter 44, which substantially eliminates the effects of ambient light, as shown in FIG. 4. The narrow pass filter 44 eliminates light having wavelengths sufficiently different from the wavelength of the light beam 50. Light beam 50 then passes through the second polarizer 46. The second polarizer 46 allows selected wavelengths of the light beam 50 that are oriented in a predefined direction to pass therethrough while preventing wavelengths oriented in a different direction to pass therethrough. In an embodiment, second polarizer 46 is oriented perpendicularly to first polarizer 40 and allows very little light to pass, except light that has been rotated by the medical fluid being tested.

The rotated portion is transmitted through the second polarizer 46 onto the photodetector 48. The transmitted portion of the light beam 50 rotates if an optically active pharmaceutical substance is present within the medical fluid, as illustrated in FIG. 4. Photodetector 48 measures the intensity of the portion of the light beam 50 projected thereon. In an embodiment, the photodetector 48 is a silicon photodiode, an array of photodiodes in a liner sensor array, or may be of another type capable of sensing and quantifying light intensity, such as a charge-coupled device (CCD). The photodetector 48 converts the portion of light beam 50 transmitted through the second polarizer 46 into an output signal corresponding to the intensity of the light. The output signal is sent from the photodetector 48 to computer 54 for a matching check to determine the quality of the medical fluid. The amount of light beam 50 projected onto the photodetector 48 is proportional to the degree of rotation of light beam 50 caused by the optically active pharmaceutical substance within the medical fluid.

Figure 5A:
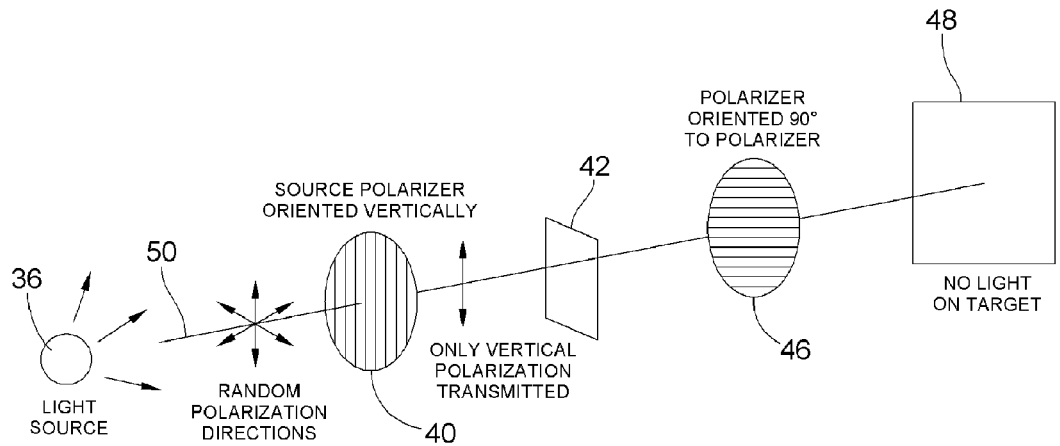
FIG. 5A is a diagram of the testing mechanism of FIG. 4 in operation.
Figure 5B:
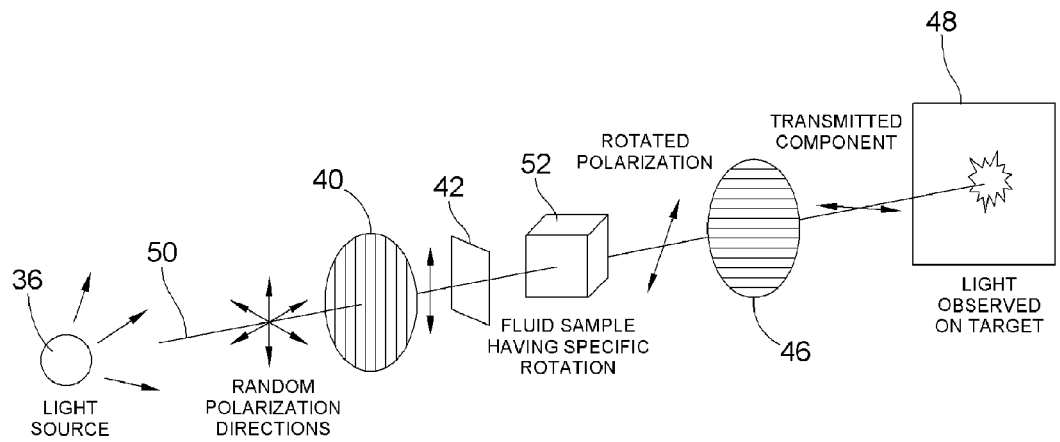
FIG. 5B is another diagram of the testing mechanism of FIG. 4 in operation.

FIGS. 5A and 5B further illustrate the first and second polarizers 40, 46 of the testing mechanism 32 performing a test in situations with and without a medical fluid having an optically active pharmaceutical substance present. FIG. 5A illustrates an embodiment of the testing mechanism 32 in which there is no material or fluid located between the polarization rotator 42 and the second polarizer 46. Alternatively, FIG. 5A illustrates the effects on the light beam 50 transmitted through a material or substance, such as a cassette or a medical fluid, lacking an optically active material or pharmaceutical substance located between the polarization rotator 42 and the second polarizer 46. The light source 38 produces a randomly polarized light beam 50. The light beam 50 is transmitted through the first polarizer 40, which transmits wavelengths of a light beam 50 that are oriented in a predetermined direction. This blocks all or substantially all other orientations of the light beam 50. The light beam 50 is then transmitted through the second polarizer 46. The second polarizer 46 allows wavelengths of the light beam oriented in a substantially perpendicular manner relative to the first polarizer 40 to pass therethrough. Because the material and medical fluid located between the first and second polarizers 40, 46 lack optically active molecules that would otherwise cause rotation of the light beam 50, the wavelengths of the light beam 50 remain polarized in the predetermined orientation dictated by the first polarizer 40 and are thus blocked by the second polarizer 46 such that no light is transmitted through the second polarizer 46. That is, without optical rotation of the light beam 50, no portion of the light beam 50 is transmitted through the second polarizer 46, which indicates that no pharmaceutical substances or materials having optically active molecules are present.

In operation, the effects illustrated and described with respect to FIG. 5 can be obtained when a cassette 20 is inserted into the corresponding recessed area 22 of the dialysis machine 10. The material used to form the side walls 24 of the cassette 20 causes optical rotation of the light beam 50 as the light beam 50 is transmitted therethrough. Prior to the medical fluid 52 being transferred from the medication containers 12 to the cassette 20, the testing mechanism 32 performs a calibration step 122 (FIG. 2). In the calibration step 122, the polarization rotator 42 is activated to cause the polarized light beam 50 from the first polarizer 40 to rotate about the propagation axis 77 an equal amount and in an opposite direction relative to the optical rotation caused by the light beam 50 passing through the side walls 24 of the cassette 20. In other words, the polarization rotator 42 offsets the optical rotational effects on the light beam 50 caused by the material of the side walls 24 of the cassette 20. The polarization rotator 42 rotates the orientation of the wavelengths of the light beam 50 such that the combined effects of the light beam passing through the polarization rotator 42 and the side walls 24 of the cassette 24 results in the wavelengths of the light beam 50 being oriented in substantially the same orientation as the wavelengths transmitted from the first polarizer 40. In an embodiment, the polarization rotator 42 is integrated with the light source 36 to produce a polarized light beam 50 in which the wavelengths of the light beam are oriented in a predetermined and adjustable direction. In the calibration step 122, the polarization rotator 42 works in conjunction with the photodetector 48 to minimize the amount of the light beam 50 that is transmitted through the second polarizer 46 onto the photodetector resulting from the optical rotation caused by the material of the side walls 24. As a result, substantially no portion of the light beam 50 transmitted from the light source 38 is transmitted onto the photodetector 48 upon completion of the calibration step 122. A memory (not illustrated) stores baseline values relating to the amount of corrective optical rotation by the polarization rotator 42 and the intensity of light that the photodetector 48 receives. Once the optimal counter-rotation of the light beam 50 about the propagation axis 77 has been determined and the baseline values are stored, medical fluid 52 is introduced into the cassette 20 to prime the cassette.

FIG. 5B illustrates the effects of an optically active substance, such as a cassette 20, a fluid containing an optically active pharmaceutical substance, or both, on the light beam 50. In the illustrated embodiment, the testing mechanism 32 tests a medical fluid for an optically active particular pharmaceutical substance such as glucose. Glucose molecules are chiral, meaning that the three-dimensional structure of the molecules are non-symmetrical and exhibit a certain "handedness." Because of the handedness of the glucose molecules, glucose is an optically active pharmaceutical substance that has the ability to rotate the orientation of polarized light relative to the propagation axis of the light that is passed through a solution containing glucose molecules. Glucose is a commonly dispensed pharmaceutical substance that is optically active. Other optically active pharmaceutical substances that can be tested using the testing mechanism 32 include, but not limited to, albumin, Factor-VIII, amino acids, sucrose, cholesterol, penicillin, camphor, taxol, and icodextrin. An example of a non-optically active solution is the buffer solution that is mixed with the glucose solution in a dual chamber, peel seal bag used for a dialysis treatment.

Glucose has a specific rotation of 52.7° for a pathlength of 100 mm at a concentration of 1 gram per ml using a light beam having a wavelength of 589 nm. The specific rotation angle will increase with a decrease in the wavelength of the light beam. The testing process in one embodiment holds constant the pathlength between the light source 38 and the photodetector 48, the wavelength of the light beam 50 generated by the light source 38, and the particular pharmaceutical substance being measured. The amount of the optically active pharmaceutical substance present in the medical fluid is proportional to the intensity of light transmitted through the second polarizer 46 onto the photodetector 48.

After the medical fluid 52 is introduced into the cassette 20, the testing mechanism 32 tests the medical fluid 52 for the presence or absence of an optically active pharmaceutical substance within the medical fluid, as indicated as step 126 (FIG. 2). Once the cassette 20 is primed, if there are no optically active molecules within the medical fluid, the photodetector 48 registers no change in intensity of light transmitted thereon relative to the baseline value stored during the calibration step 122 explained above with respect to FIG. 5A. No change in the intensity of light measured by the photodetector 48 indicates that the medical fluid tested does not have a significant amount of molecules of the particular optically active pharmaceutical substance. This may be caused by a lack of optically-active molecules in the medical fluid or by failure to properly mix the medical fluid. If there are no optically active pharmaceutical substances in the medical fluid, the computer 54 of the testing mechanism 32 generates an output signal to the medication delivery system to provide an alert to the user or to prevent the medical fluid from being delivered to the patient. If the photodetector 48 detects a change in the intensity of light transmitted through the second polarizer 46, the computer 54 provides an output signal to the testing mechanism 32 to perform a test to determine the concentration of the pharmaceutical substance within the medical fluid, as indicated in step 130 (FIG. 2).

In operation, once the medical fluid 52 has primed the cassette 20, the testing mechanism 32 performs a test by emitting a light beam 50 from the light source 38 through the cassette 20 and medical fluid 52. A change in the intensity of the light that the photodetector 48 receives from the baseline values indicates the presence of an optically active pharmaceutical substance within the medical fluid. The relative change in intensity of light received by the photodetector 48 is proportional to the concentration of the pharmaceutical substance within the medical fluid. The photodetector 48 provides an output signal to the computer 54 indicating the measured light intensity. The computer then calculates the concentration of the pharmaceutical substance within the medical fluid based upon the measured intensity of light transmitted onto the photodetector 48. The computer 54 performs a matching check with a look-up table stored in a database to determine if the concentration of the pharmaceutical substance within the medical fluid, based upon the difference in light intensity relative to the baseline measurement, is within a desired, or acceptable, range for the concentration, as indicated in step 134 (FIG. 2). If the concentration of the pharmaceutical substance within the medical fluid is outside an acceptable range, the computer provides an output signal to the medication delivery system to provide an alarm or to prevent the medical fluid from being delivered to the patient, as indicated in step 132 (FIG. 2). If the concentration of the pharmaceutical substance within the medical fluid is within an acceptable range, the computer provides an output signal to the medication delivery system to proceed with normal functioning of the medical delivery system. In one embodiment, the testing mechanism 32 performs the tests of steps 126 and 130 only once when the cassette 20 is being primed. In another embodiment, the testing mechanism 32 continuously performs the tests of steps 126 and 130 at regular intervals while the medical fluid is being delivered to the patient to ensure the proper concentration of the pharmaceutical substance is delivered to the patient.

In the embodiment illustrated in FIG. 4, the testing mechanism operates with a medication delivery system to test for the presence and concentration of an assumed pharmaceutical substance in the medical fluid being delivered to the patient. In an exemplary embodiment, the testing mechanism 32 is incorporated within the dialysis machine 10 to test for the presence or absence, and preferably the concentration, of glucose molecules in the medical fluid being delivered to a patient.

The testing mechanism 32 illustrated in FIG. 4 uses optical polarization rotation to determine the presence or absence of glucose molecules, or other optically active pharmaceutical substances, within the medical fluid being delivered to the patient. As a light beam propagates through an optically active medical fluid, the orientation of the polarized light beam is rotated some angle about the propagation axis 77. The amount of rotation is a function of the pathlength through the medical fluid, the concentration of the optically active pharmaceutical substance, and the specific rotation of the pharmaceutical substance. If a larger angle of rotation resulting from the optically active pharmaceutical substance is required to detect a change in intensity of light received by the photodetector 48, the wavelength of the light beam 50 should be decreased or the pathlength between the light source 38 and the photodetector 48 should be increased.

The process of FIG. 2, and the corresponding testing mechanism 32 illustrated in FIGS. 3A to 3D, 4, and 5A to 5B, determines the presence or absence and the concentration of a particular optically active pharmaceutical substance within a medical fluid. Although the illustrated testing mechanism 32 performs a test in which the pharmaceutical substance is assumed, the testing mechanism can alternatively or additionally allow the user to specify a particular pharmaceutical substance or substances to be tested. In another embodiment, the testing mechanism 32 first performs a test to identify each optically active pharmaceutical substance present within the medical fluid.

Figure 6:
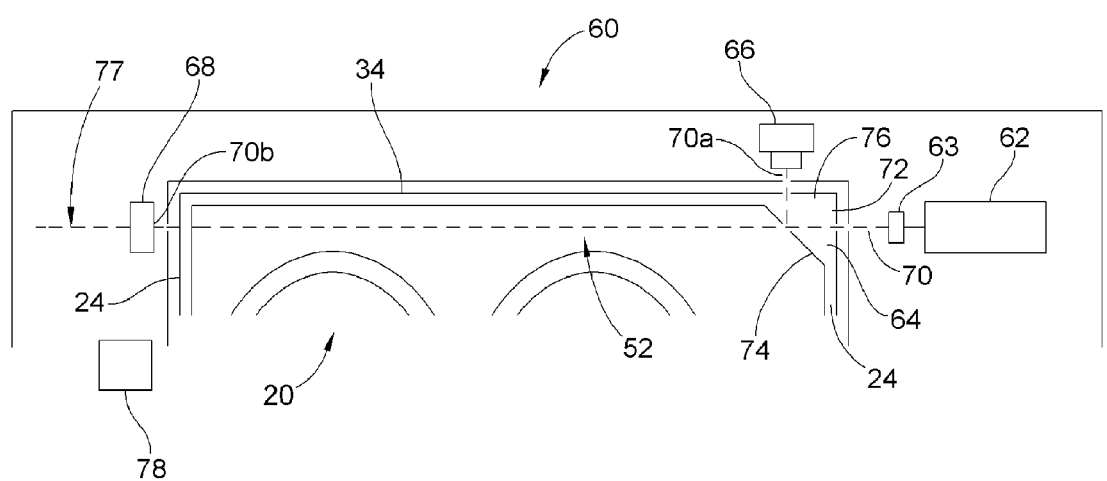
FIG. 6 is a cross sectional view of the cassette of FIG. 3D along line IV-IV and another embodiment of a testing mechanism.

Another embodiment of a non-invasive testing mechanism 60 integrated within a medication delivery system is illustrated in FIG. 6. In this embodiment, the testing mechanism 60 is incorporated within a disposable housing that forms a part of a disposable line set 14 connecting a medication container 12 to a medication delivery system. The testing mechanism 60 illustrated in FIG. 6 can be incorporated into a dialysis machine 10, such as the one described above and illustrated in FIGS. 3A to 3D. In an embodiment, the testing mechanism 60 uses refractometry to determine the presence or absence of a pharmaceutical substance, identify each pharmaceutical substance present in the medical fluid, and measure the concentration of each pharmaceutical substance in the medical fluid. The testing mechanism 60 includes a light source 62, a polarization rotator 63, a prism 64, a first photodetector 66 for receiving and measuring reflected light, and a second photodetector 68 for receiving and measuring refracted light. In an embodiment, the light source 62 is a laser that provides a light beam 70 directed into prism 64. In another embodiment, the light source 62 is a light emitting diode ("LED"). In yet another embodiment, the light source 62 is a fluorescent light, or any other type of light capable of producing a light beam 70. It should be understood by one skilled in the art that any light source, such as a laser or LED, capable of producing a narrow beam of light can be used.

It is also possible to discern between fluids, or concentrations within fluids, by measuring the intensities of the reflected and transmitted beams of light. Another technique uses the refraction index of solutions and the principles embodied in the Fresnel equations. These equations can be used to determine the refractive index of a solution, if the reflection coefficients, the fraction of incident light reflected, and the incidence/refraction angles are known. The Fresnel equations are $$R_p = [(n_1 \cos(\theta_2) - n_2 \cos(\theta_1))/(n_1 \cos(\theta_2) + n_2 \cos(\theta_1))]^2 \quad \text{(Equation 3) and}$$

$$R_s = [(n_1 \cos(\theta_1) - n_2 \cos(\theta_2))/(n_1 \cos(\theta_1) + n_2 \cos(\theta_2))]^2 \quad \text{(Equation 4)}.$$

Where $R_p$ and $R_s$ are the reflection coefficients for parallel and perpendicular polarized light respectively. The angles of refraction for the transmitted beam are determined from Snell's law above (Equation 1). The transmission coefficients are determined from the reflection coefficients by $$T_s = 1 - R_s \quad \text{(Equation 5) and}$$

$$T_p = 1 - R_p \quad \text{(Equation 6)}$$

Based on these equations, and since the total incident beam is split into the reflected and refracted components, a variety of refractive index measurement techniques are possible by measuring the direction or intensity, or both, of the reflected and transmitted beams with photodetectors placed at appropriate locations to receive the reflected and refracted beams.

In yet another embodiment, a polarized light source, such as a polarized laser, may be used with polarization rotator 63, to enhance the sensitivity of the testing machine. Equations (3) through (6) may be used with the polarization rotator 63 and first photodetector 66 for detecting reflected light and thus the concentration of medical fluid in the cassette when the total incident beam is split only into reflected and refracted components.

Light source 62 is located adjacent side wall 24 of cassette 20 disposed within dialysis machine 10. The light source 62 projects a light beam 70 into prism 64, as shown in FIG. 6. In one embodiment, prism 64 is molded into a disposable medical fluid chamber, such as a disposable cassette 20 (FIGS. 3C and 3D), used in a peritoneal dialysis machine 10. Incidence surface 72 of prism 64 may be oriented normal to axis of propagation 77 of light beam 70. Interface surface 74 provides an interface between the prism 64 and the interior of the cassette 20 through which a medical fluid 52 can flow. In one embodiment, interface surface 74 of prism 64 is oriented at a 45° degree angle relative to incidence surface 72. In another embodiment, the interface surface 74 is oriented at Brewster's angle relative to the incidence surface 72, as explained below. It will be understood by one skilled in the art that interface surface 74 may be oriented at any angle relative to incidence surface 72 sufficient to allow for at least partial transmission of light beam 70 through interface surface 74. When a medical fluid is present within the cassette 20, the interface surface 74 is in fluid communication with the medical fluid. In other embodiments, a container for the medical fluid, or tubing leading from a container for the medical fluid, such as tubing from an IV bag, may be adjacent interface surface 74.

In an embodiment, prism 64 and cassette 20 are integrally formed, as illustrated in FIG. 6. Cassette 20 and prism 64 are preferably formed of a polymer having a refractive index of about 1.5. This includes many common polymers, such as polyethylene, polypropylene, polymethylmethacrylate, acetal, nylon, cellulose acetate, cellulose acetate butyrate, and so forth. In another embodiment, the cassette 20 and prism 64 are formed separately and later attached to form a unitary member. The prism 64 and cassette 20 can be formed of different materials, but the refractive indices for each material should be taken into consideration when aligning the components of the testing mechanism 60 for proper measurements.

In one embodiment, the first photodetector 66 is located adjacent to the reflection surface 76 of the prism 64, as shown in FIG. 6. Reflection surface 76 is oriented substantially perpendicular relative to the incidence surface 72, and light reflected from incidence surface 72 may exit through reflection surface 76 for detection by a photodetector. In one embodiment, the first photodetector 66 is a silicon photodiode. In another embodiment, the first photodetector 66 is a linear photodetector array. It should be understood by one skilled in the art that the first photodetector 66 may be any sensing mechanism capable of detecting the intensity and position of the portion of light beam 70a reflected from prism 64. First photodetector 66 receives the portion of light beam 70a reflected by the interface surface 74. First photodetector 66 generates an output signal to computer 78 that corresponds to the measured intensity of the reflected light beam 70a.

As depicted in FIG. 6, second photodetector 68 is located adjacent to the side wall 24 on the far side of cassette 20, opposite side wall 24 adjacent to light source 62. In an embodiment, the second photodetector 68 is a silicon photodiode. In another embodiment, the second photodetector 68 is a linear photodetector array. It should be understood by one skilled in the art that the second photodetector 68 may be any sensing mechanism capable of detecting the intensity and position of the portion of the light beam 70 that is transmitted through the prism and the medical fluid, light beam 70b. The second photodetector 68 receives the portion of the light beam 70 that interface surface 74 refracts and transmits through the medical fluid 52, i.e. light beam 70b. The second photodetector 68 generates an output signal to computer 78 that corresponds to the measured intensity and position of the refracted portion light beam 70b onto the second photodetector 68. Both the first and second photodetectors 66, 68 are operatively connected to computer 78.

Prior to the cassette 20 being primed, the fluid within the cassette 20 is air. The refractive index of air is about 1.0. During the calibration step 122 (FIG. 2), there is desirably a large difference between the refractive index of the prism 64 and the refractive index of air which causes the light beam 70 to be reflected toward the outer wall 34 of the cassette 20, e.g. portion 70a. In an embodiment, before the cassette 20 is primed, portion 70b of light beam 70 is transmitted through the prism 64 and side wall 24 onto the second photodetector 68. The relative position of the transmitted light beam 70b measured by the second photodetector 68 during the calibration step 122 provides the baseline measurement for later comparison with measurements of the transmitted light beam 70b within a medical fluid 52. As medical fluid is added to the cassette 20 during the priming step 124, the difference between the refractive indices at the interface surface 74 decreases, which results in less refraction of light beam 70b transmitted onto second photodetector 68. As the difference in the refractive indices at the interface surface 74 decreases, the intensity of the light received by the second photodetector 68 increases. The second photodetector measures the relative location of the portion of the refracted light beam 70b and generates an output signal to the computer 78 representing the intensity and relative change in location of the light beam 70b. At the same time, the first photodetector 66 measures the intensity and relative position of the reflected light beam 70a and generates an output signal to the computer 78 representing the intensity and relative position of the received light beam 70a. The computer 78 receives the output signal from both the first and second photodetectors 66, 68 and performs a matching check using these output signals. These results may be used in combination with the Fresnel equations above to determine the concentration of medical fluid within cassette 20.

In operation, the computer 78 receives the output signals from the first and second photodetectors 66, 68. The computer 78 performs a calculation to determine the refractive index of the medical fluid 52 based upon the measured changes resulting from the introduction of the medical fluid into the cassette 20. The computer 78 then determines the concentration of the pharmaceutical substance within the medical fluid based upon the calculated refractive index. In an embodiment, the wavelength of the light beam 70 is varied, thereby producing different and distinct output signals to the computer 78 from the first and second photodetectors 66, 68. The computer 78 performs a matching check by comparing the calculated concentration of the pharmaceutical substance with values in a look-up table located in a database.

If the computer 78 determines the presence of a pharmaceutical substance that is not intended to be in the medical fluid, the computer generates an output signal to the medication delivery system to provide an alert to the user or to prevent delivery of the medical fluid to the patient. Also, if the computer determines that the concentration of a pharmaceutical substance within the medical fluid is outside an acceptable concentration range, the computer generates an output signal to provide an alert to the user or to prevent delivery of the medical fluid to the patient.

In another embodiment, the interface surface 74 may be oriented at an angle other than 45°, e.g., Brewster's angle. Brewster's angle is the angle at which linearly polarized light has maximum transmission when the polarization direction of the light is parallel to the plane of incidence with the prism. If the angle of the interface surface 74 of the prism 64 is oriented at Brewster's angle, there will be total transmission of the light beam 70 into the medical fluid 52 if the medical fluid possesses the target refractive index. Brewster's angle is measured as: $\theta_B = \arctan(n_2/n_1)$ wherein $n_1$ is the refractive index of the prism and $n_2$ is the refractive index of the medical fluid. For example, given a properly mixed solution of dialysate having a refractive index of 1.34 and a polymeric prism 64 having a refractive index of 1.5, Brewster's angle is 44.78°. In operation, the interface surface 74 of the prism 64 is aligned at 44.78° relative to the propagation axis 77 of the light beam 70 such that the entire portion of the light beam 70 is transmitted through the medical fluid 52.

When the interface surface 74 of the prism 64 is aligned at Brewster's angle, total transmission of the light beam 70 through the medical fluid 52 should be produced. Prior to the introduction of a medical fluid, baseline measurements are determined by the second photodetector 68 during the calibration step 122 (FIG. 2). If the concentration of the medical fluid 52 changes during delivery to the patient, the relative position of the transmitted light beam 70 moves along the second photodetector 68 and the intensity of the detected light changes. In operation, a measured change in the intensity or relative position of the transmitted light beam 70 relative to a baseline measurement and intensity causes the second photodetector 68 to generate an output signal to the computer 78 to indicate a change in the concentration of the pharmaceutical substance. The computer 78 then generates an output signal to the medication delivery system to provide an alert or to prevent delivery of the medical fluid 52 to the patient.

Figure 7:
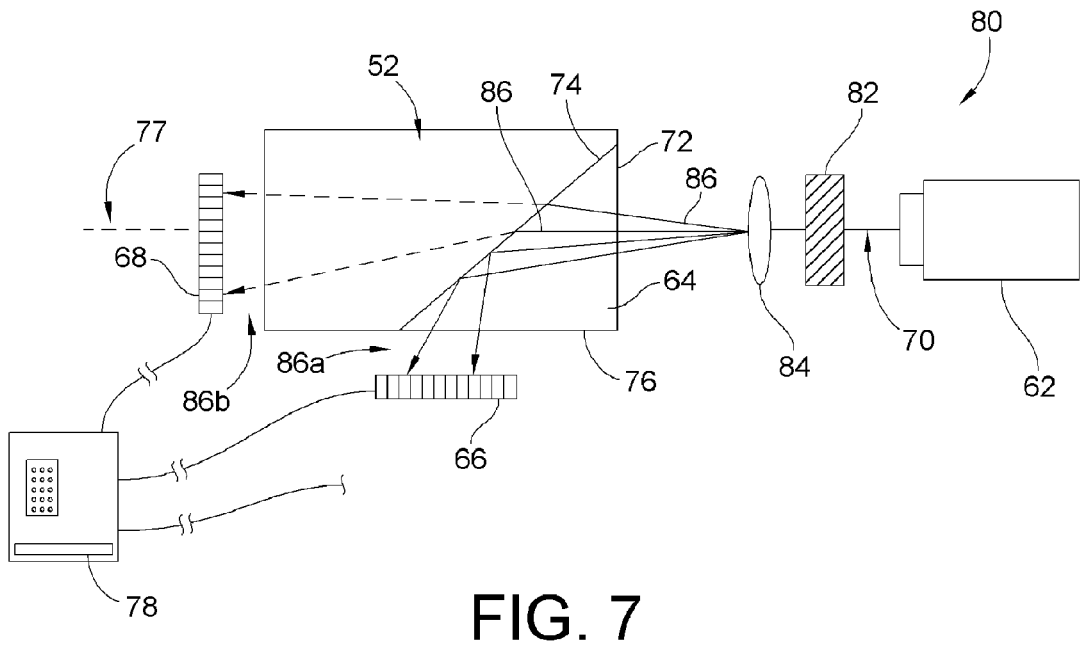
FIG. 7 is a cross sectional view of yet another embodiment of a testing mechanism in operation.

The testing mechanism 80 of FIG. 7 illustrates another embodiment of a testing mechanism to test the medical fluid 52 using refractometry. The testing mechanism 80 includes a light source 62, a prism 64, a first photodetector 66, a second photodetector 68, a polarization rotator 82, and a beam expanding lens 84. In an embodiment, the first and second photodetectors 66, 68 are linear photodetector arrays capable of measuring both the intensity and the position of the light.

In an embodiment, the polarization rotator 82 is a liquid crystal device. The polarization rotator 82 rotates the polarization orientation of the light beam 70 to compensate for the rotational effects on the light beam caused by the material of the prism 64, as explained above. The polarization rotator 82 rotates the orientation of the light beam 70 an equal amount and in the opposite direction relative to the optical rotation expected to be caused by the material or materials used in the prism 64 and cassette 20. The polarization rotator 82 allows the light beam 70 to be polarized to ensure that the polarization direction of the light beam 70 is oriented parallel or perpendicular to the interface surface 74 of the prism 64.

The beam expanding lens 84 receives the polarized light beam 70 from the polarization rotator 82 and spreads the light beam 70 into multiple rays 86 of light in a plane parallel to the plane of incidence, that are transmitted to the interface surface 74 of the prism 64, as illustrated in FIG. 7. Each of the rays 86 is reflected and refracted differently depending upon the difference in refractive indices at the interface surface 74 and the angle of incidence between each ray 86 and the interface surface 74. The first linear photodetector array 66 measures the intensity and relative position of reflected light 86a, and the second linear photodetector array 68 measures the intensity and relative position of refracted light 86b. The first and second linear photodetector arrays 66, 68 are operatively connected to a computer (89), and photodetector arrays 66, 68 provide an output signal correlating to the measured intensity and relative position measured from detected light 86a, 86b. A more refined refractive index calculation is obtainable using the measurements of intensity and relative position of the reflected and refracted portions of light beam 70 by both linear photodetector arrays 66, 68.

Another embodiment uses the finely divided surface of a diffraction grating to increase the sensitivity of the measurements. When a light beam is incident on a grating with an angle $\theta_i$ (measured from the normal of the grating), it is diffracted into several beams. The beam that corresponds to direct transmission is called the zero order, and is denoted by m=0. The other orders correspond to diffraction angles which are represented by non-zero integers m. For a groove period d and an incident wavelength λ, the grating equation gives the value of the diffracted angle $\theta_m(\lambda)$ in the order m:

$$d(\sin \theta_m(\lambda) + \sin \theta_i) = m\lambda \qquad \text{(Equation 7)}$$

Figure 8:
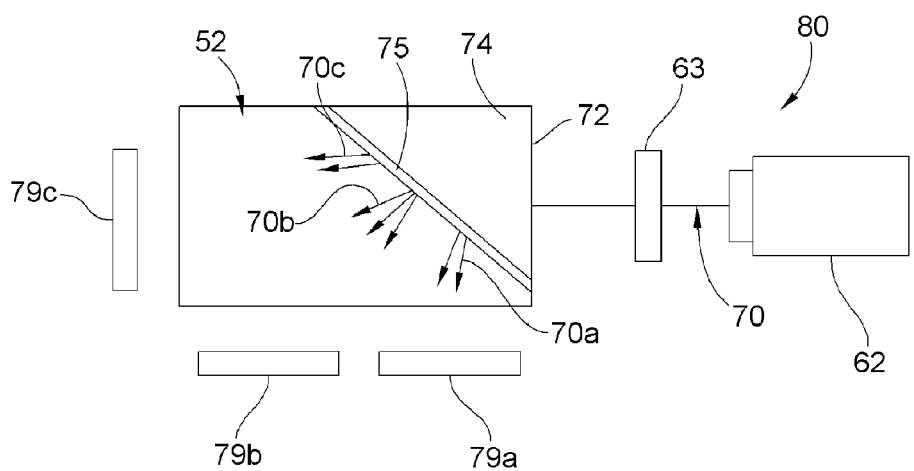
FIG. 8 is a cross sectional view of an embodiment using a diffraction grating.

Using this equation for a series of orders m, the angle of diffracted light can be predicted and then correlated with a concentration of a substance in a medical fluid, as seen above in FIGS. 1B and 1C. An embodiment using this principle is depicted schematically in FIG. 8. A light source 62, preferably a laser light source, emits a light beam 70 which may be polarized by an optical polarizer 63. The light beam strikes prism 74, whose opposite surface, normally the interface surface with medical fluid 52, has been made into a refractive diffraction grating 75 with a large number of fine lines on its outer surface. Some diffraction gratings do not use physical grooves but instead use a gel with a periodic modulation of the refractive index within the gel. These volume phase holography diffraction gratings are typically contained between two substrates for environmental resistance and long life. These are among the diffraction gratings that may be used in embodiments of the invention, but are not preferred because their performance depends more on local conditions of temperature and humidity than standard diffraction gratings. The light is diffracted in conformity with the construction of the diffraction grating, and then further refracted by the medical fluid 52 through which the light passes in its way to one or more photodetectors 79a, 79b, 79c. In this embodiment, photodetector arrays 70a, 70b, 70c receive and detect respectively reflected, refracted, and transmitted light 70a, 70b, 70c.

Figure 9:
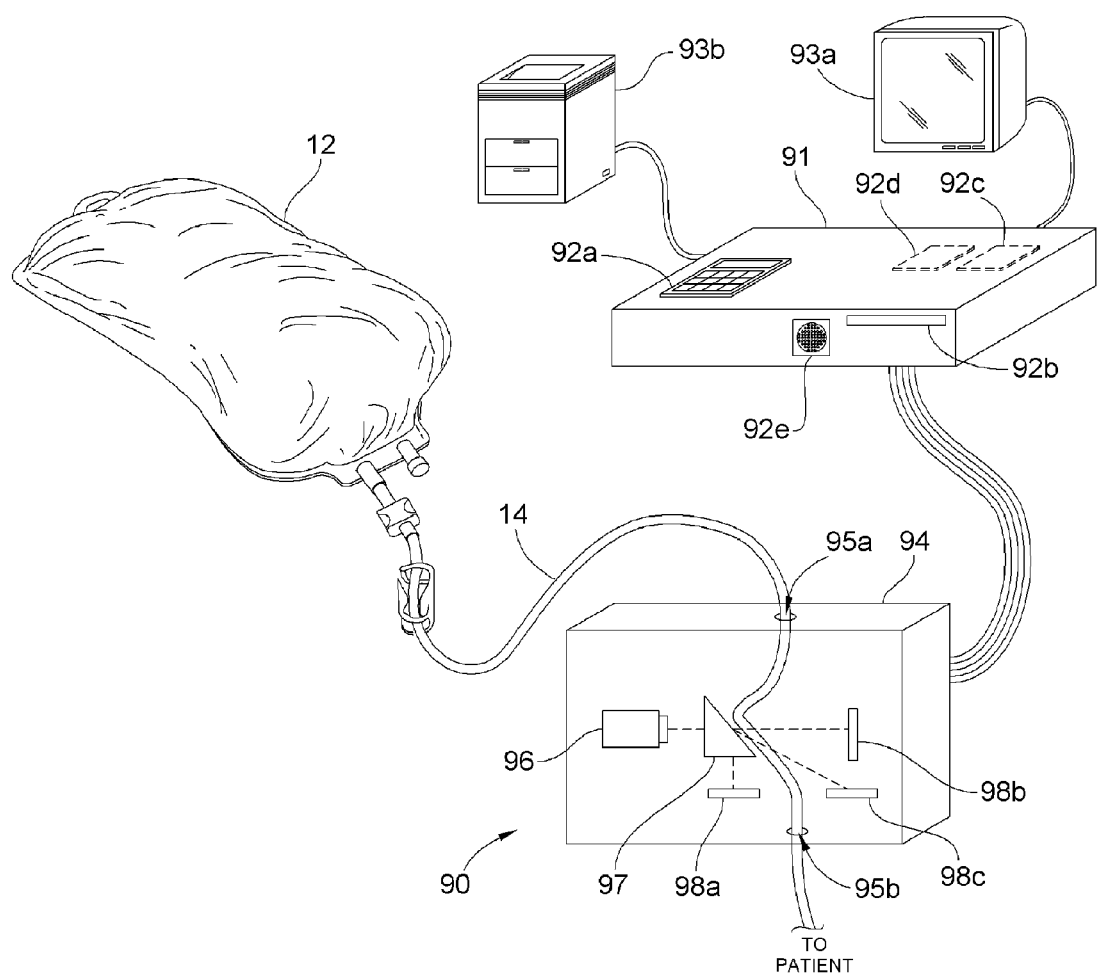
FIG. 9 is a perspective view of another embodiment of a testing mechanism.

The principles described above are not limited to dialysis machines or fluids. Another embodiment is depicted in FIG. 9, in which a container with a medical fluid 12 is analyzed for its contents before it is administered to a patient. An example may be a fluid intended for intravenous administration to a patient, such as a medication in saline solution, or a nutritional fluid. In this embodiment, the bag may be gently massaged so that its contents are well-mixed, and tubing 14, part of the medical delivery system, is then led through an analysis machine or computer 90 with housing 94. The computer includes a microprocessor 92c and a memory 92d accessible to the microprocessor. The computer also includes an ingress port 95a and an egress port 95b to seal out ambient light. The machine includes a light source 96, a prism 97, and one or more photodetectors 98a, 98b, 98c, to detect the behavior of light as it is affected by the medical fluid. Signals from the photodetectors are led into computer 91 for analysis and results. The computer has at least one input, such as a keyboard or input pad 92a and also a second input 92b for a floppy disc or CD, for input or output. The computer also has an output monitor 93a and a printer 93b for creating a permanent record. Alerts or alarms may be issued through the computer outputs, including a speaker 92e.

In one embodiment, the medical fluid remains in the tubing, which is placed in intimate contact with the prism. The tubing and the incident light are both presented at an angle to the light beam. This embodiment can be used with both optical rotation and refractive index measurements.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A medical fluid delivery system comprising:
a medical fluid delivery machine for delivering a medical fluid, the medical fluid delivery machine including a light source configured to generate a light beam;
a polarizer configured to receive the light beam and to allow a portion of the light beam to be transmitted through the polarizer;
a photodetector configured to provide a measurement of an intensity of the light beam transmitted through the medical fluid and the polarizer;
a medical fluid cassette operating with the medical fluid delivery machine to pump the medical fluid, the medical fluid cassette including a rigid structure defining a fluid passageway located between first and second light-transmissive sides of the medical fluid cassette, the cassette further including a pumping portion in fluid communication with the fluid passageway, the medical fluid cassette loaded onto the medical fluid delivery machine such that (i) the light source resides on the first side of the cassette, (ii) the photodetector resides on the second side of the cassette, and (iii) the light beam from the light source is transmitted into the passageway of the cassette; and
a computer configured to use the measurement of the intensity to determine whether the medical fluid can be delivered to a patient.

2. The medical fluid delivery system of claim 1, which includes a prism, the photodetector receiving a portion of the light beam refracted from the prism.

3. The medical fluid delivery system of claim 2, wherein the prism and the fluid cassette are integrally formed.

4. The medical fluid delivery system of claim 2, wherein the photodetector is a first photodetector, which includes a second photodetector, and wherein the first photodetector is positioned to receive and measure an intensity of light from the light beam that is transmitted through the prism and the second photodetector is positioned to receive and measure an intensity of light from the light beam that is reflected or refracted by the prism or by the prism and the medical fluid.

5. The medical fluid delivery system of claim 2, wherein an interface surface of the prism is oriented at an angle to the light beam selected from the group consisting of forty-five degrees and Brewster's angle.

6. The medical fluid delivery system of claim 1, wherein the medical fluid delivery machine further includes a polarization rotator disposed between the light source and the medical fluid cassette.

7. The medical fluid delivery system of claim 6, wherein the polarization rotator is a first polarization rotator, and which includes a second polarization rotator disposed between the medical fluid cassette and the photodetector.

8. The medical fluid delivery system of claim 1, wherein the polarizer is positioned between the medical fluid cassette and the photodetector.

9. The medical fluid delivery system of claim 1, wherein the polarizer is a first polarizer, and which includes a second polarizer positioned between the light source and the medical fluid cassette, wherein the second polarizer is at least one of (i) configured to polarize the light beam prior to the light beam being transmitted through the medical fluid; and (ii) configured to polarize the light beam at a ninety degree angle relative to the first polarizer.

10. The medical fluid delivery system of claim 1, wherein the medical fluid cassette is disposable.

11. The medical fluid delivery system of claim 1, wherein the medical fluid cassette is removably positioned within a recess of the medical fluid delivery machine, and wherein the light source is positioned adjacent to the recess of the medical fluid delivery machine, such that the light source is positioned to transmit the light beam through the passageway of the medical fluid cassette.

12. The medical fluid delivery system of claim 1, wherein the medical fluid delivery machine further includes a narrow pass filter configured to filter out ambient light or to pass a particular light wavelength.

13. The medical fluid delivery system of claim 12, wherein the narrow pass filter is positioned between the medical fluid cassette and the photodetector.

14. The medical fluid delivery system of claim 1, wherein the computer is configured to perform a matching check to determine if or how much of a pharmaceutical substance is present in the medical fluid.

15. The medical fluid delivery system of claim 14, wherein the computer is configured to generate an output signal to provide an alert or to prevent the medical fluid delivery system from delivering the medical fluid to the patient if the matching check determines that the pharmaceutical substance is present in the medical fluid in a concentration higher or lower than expected.

16. The medical fluid delivery system of claim 1, wherein the computer is at least one of:
   (i) configured to utilize the measurement of intensity to calculate a concentration of a pharmaceutical substance within the medical fluid;
   (ii) configured to include a memory having a look-up table stored therein, wherein the look-up table includes an acceptable range of calculated concentrations of the pharmaceutical substance within the medical fluid;
   (iii) configured to be operatively connected to an externally located database having a look-up table stored therein, wherein the look-up table includes an acceptable range of calculated concentrations of the pharmaceutical substance within the medical fluid;
   (iv) configured to generate an output signal to the medical fluid delivery system to provide an alert or to prevent the medical fluid from being delivered to the patient if the calculated concentration of the pharmaceutical substance is outside an acceptable range; or
   (v) configured to generate an output signal to the medical fluid delivery system to proceed with normal function if the calculated concentration of the pharmaceutical substance is within an acceptable range.

17. The medical fluid delivery system of claim 1, where the medical fluid delivery machine is a dialysis machine or a drug delivery machine.

18. A medical fluid delivery system comprising:
   a medical fluid delivery machine including a laser beam light source configured to generate a laser beam;
   a medical fluid cassette operating with the medical fluid delivery machine to pump a medical fluid, the medical fluid cassette including a rigid structure defining a fluid passageway located between first and second light-transmissive sides of the medical fluid cassette, the cassette further including a pumping portion in fluid communication with the fluid passageway, the medical fluid cassette loaded onto the medical fluid delivery machine such that (i) the laser beam light source resides on the first side of the medical fluid delivery cassette and (ii) a photodetector resides on the second side of the medical fluid delivery cassette, the photodetector configured to provide a measurement of an intensity of the laser beam transmitted through the medical fluid flowing through the passageway of the medical fluid cassette; and
   a computer configured to use the measurement of the intensity to determine whether the medical fluid can be delivered to a patient.

19. A medical fluid delivery system comprising:
   a medical fluid delivery machine for delivering a medical fluid, the medical fluid delivery machine including a light source configured to generate a light beam;
   a polarizer configured to receive the light beam and to allow a portion of the light beam within the medical fluid to be transmitted through the medical fluid and the polarizer;
   a photodetector configured to provide a measurement of an intensity of the light beam transmitted through the medical fluid and the polarizer;
   medical fluid tubing operating with the medical fluid delivery machine to pump the medical fluid, the medical fluid tubing loaded onto the medical fluid delivery machine adjacent the polarizer, such that the light source resides on a first side of the medical fluid tubing and the photodetector resides on a second side of the medical fluid tubing, wherein the light beam from the light source is transmitted through the medical fluid tubing; and
   a computer configured to use the measurement of the intensity to determine whether the medical fluid can be delivered to a patient.

20. The medical fluid delivery system of claim 19, where the medical fluid delivery machine is a dialysis machine or a drug delivery machine.

21. A dialysis system comprising:
   a dialysis machine for delivering a dialysis fluid, the dialysis machine including a light source configured to generate a light beam;
   a polarizer configured to receive the light beam and to allow a portion of the light beam within the dialysis fluid to be transmitted through the polarizer;
   a photodetector configured to provide a measurement of an intensity of the light beam transmitted through the medical fluid and the polarizer;
   a dialysis fluid cassette operating with the dialysis machine to pump the dialysis fluid, the dialysis fluid cassette including a rigid structure defining a fluid passageway located between first and second light-transmissive sides of the dialysis fluid cassette, the cassette further including a pumping portion in fluid communication with the fluid passageway, the dialysis fluid cassette loaded onto the dialysis machine such that (i) the light source resides on the first side of the dialysis fluid cassette, (ii) the photodetector resides on the second side of the dialysis fluid cassette, and (iii) the light beam from the light source is transmitted into the passageway of the cassette; and
   a computer configured to use the measurement of the intensity to determine whether the dialysis fluid can be delivered to a patient.

22. A drug delivery system comprising:
   a drug delivery machine for delivering a drug, the drug delivery machine including a light source configured to generate a light beam;
   a polarizer configured to receive the light beam and to allow a portion of the light beam within the drug to be transmitted through the polarizer;
   a photodetector configured to provide a measurement of an intensity of the light beam transmitted through the drug and the polarizer;
   a drug delivery cassette operating with the drug delivery machine to pump the drug, the drug delivery cassette including a rigid structure defining a fluid passageway located between first and second light-transmissive sides of the drug delivery cassette, the cassette further including a pumping portion in fluid communication with the fluid passageway, the drug delivery cassette loaded onto the drug delivery machine such that the light source resides on the first side of the drug delivery cassette and the photodetector resides on the second side of the drug delivery cassette, wherein the light beam from the light source is transmitted through the passageway of the cassette; and
   a computer configured to use the measurement of the intensity to determine whether the drug can be delivered to a patient.

* * * * *